US012779212B2

(12) United States Patent
Deslauriers

(10) Patent No.: US 12,779,212 B2
(45) Date of Patent: Nov. 3, 2026

(54) TRANSDUCER ARRAYS HAVING ALTERNATIVE ARRAY MATERIALS

(71) Applicant: Novocure GmbH, Root (CH)

(72) Inventor: Richard Deslauriers, Woodbury, CT (US)

(73) Assignee: Novocure GmbH, Baar (CH)

( * ) Notice: Subject to any disclaimer, the term of this patent is extended or adjusted under 35 U.S.C. 154(b) by 260 days.

(21) Appl. No.: 18/523,221

(22) Filed: Nov. 29, 2023

(65) Prior Publication Data

US 2024/0173544 A1 May 30, 2024

Related U.S. Application Data

(60) Provisional application No. 63/385,540, filed on Nov. 30, 2022.

(51) Int. Cl.

*A61N 1/04* (2006.01)
*A61N 1/36* (2006.01)
*A61N 1/40* (2006.01)

(52) U.S. Cl.

CPC ......... *A61N 1/0496* (2013.01); *A61N 1/0476* (2013.01); *A61N 1/36002* (2017.08); *A61N 1/40* (2013.01)

(58) Field of Classification Search

None

See application file for complete search history.

(56) References Cited

U.S. PATENT DOCUMENTS 5,330,527 A * 7/1994 Montecalvo ............. A61N 1/04 600/397
9,818,499 B2 11/2017 Burnham et al.
(Continued)

FOREIGN PATENT DOCUMENTS

CN 1310386 C 4/2007
CN 104684611 A 6/2015
WO WO 2019/115373 A1 6/2019

OTHER PUBLICATIONS

Stauffer, Flurin Samuel; “Soft and Stretchable Electronics for Interfacing Biological Tissues”, PhD Thesis, Diss. ETH No. 24825, 2018.

(Continued)

*Primary Examiner* — Michael W Kahelin
(74) *Attorney, Agent, or Firm* — DUNLAP CODDING, P.C.

(57) ABSTRACT

A transducer array, an electronic apparatus, and a method are described. The transducer array comprises an electrode assembly including an electrode layer and a non-hydrogel skin-interface material. The electrode layer comprising one or more electrode. The non-hydrogel skin-interface material is for placement between a surface of the electrode layer and a patient’s skin, the non-hydrogel skin-interface material being configured to contact the patient’s skin and to conform to contours and/or irregularities of the patient’s skin. The method includes applying a non-hydrogel skin-interface material to a patient’s skin. The non-hydrogel skin-interface material is configured to contact the patient’s skin and to conform to contours and/or irregularities of the patient’s skin. An electrode assembly is then applied to a surface of the non-hydrogel skin-interface material.

18 Claims, 3 Drawing Sheets

(56) References Cited

U.S. PATENT DOCUMENTS

| | | | | |
|---|---|---|---|---|
| 9,947,432 | B2 | 4/2018 | Burnham et al. | |
| 11,224,741 | B2 | 1/2022 | Kirson et al. | |
| 11,395,916 | B2 | 7/2022 | Wasserman et al. | |
| 11,458,298 | B2 | 10/2022 | Deslauriers | |
| 11,806,521 | B1 * | 11/2023 | Kosierkiewicz | H02N 2/18 |
| 2006/0251880 | A1 | 11/2006 | Munro et al. | |
| 2014/0073896 | A1 * | 3/2014 | Hyatt | A61N 1/0492 600/386 |
| 2015/0282312 | A1 | 10/2015 | Burnham et al. | |
| 2016/0067103 | A1 * | 3/2016 | Anthony | A61N 1/0468 607/152 |
| 2016/0250015 | A1 | 9/2016 | Kim et al. | |
| 2019/0167976 | A1 * | 6/2019 | Byers | A61N 1/0484 |
| 2020/0054218 | A1 * | 2/2020 | Xi | A61B 5/015 |
| 2021/0346693 | A1 * | 11/2021 | Deslauriers | A61N 1/36002 |
| 2023/0037806 | A1 | 2/2023 | Wasserman et al. | |
| 2023/0065587 | A1 | 3/2023 | Shnaiderman et al. | |

OTHER PUBLICATIONS

Stauffer et al., "Skin conformal Polymer Electrodes for Clinical ECG and EEG Recordings", Advanced Healthcare Materials, 1700994, 2018.

International Search Report and Written Opinion, International application No. PCT/IB2023/062033, filed Nov. 29, 2023, 15 pages.

* cited by examiner

TRANSDUCER ARRAYS HAVING ALTERNATIVE ARRAY MATERIALS

CROSS-REFERENCE TO RELATED APPLICATIONS

This application claims priority to the provisional patent application identified by U.S. Ser. No. 63/385,540, filed Nov. 30, 2022, the entire content of which is hereby expressly incorporated herein by reference.

STATEMENT REGARDING FEDERALLY SPONSORED RESEARCH OR DEVELOPMENT

Not Applicable.

BACKGROUND

Tumor Treating Fields (TTFields or TTFs) are low intensity (e.g., 1-10 V/cm) alternating electric fields within the intermediate frequency range (50 kHz to 1 MHz, such as, for example, 100-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. TTFields are approved for the treatment of glioblastoma multiforme (GBM), and may be delivered, for example, via the OPTUNE® system (Novocure Limited, St. Helier, Jersey), which includes transducer arrays to be placed on the patient's shaved head.

Conventionally, each transducer array used for the delivery of TTFields in the OPTUNE® device comprises a set of non-conductive ceramic disk electrodes, which are coupled to the patient's skin (such as, but not limited to, the patient's shaved head for treatment of GBM) through a layer of conductive medical gel, such as a hydrogel. To form the ceramic disk electrodes, a conductive layer is formed on a top surface (outwardly facing surface) of nonconductive ceramic material. A bottom surface (skin-facing surface) of the nonconductive ceramic material is coupled to the conductive medical gel.

One approach to applying the TTField in different directions is to apply the field between a first set of electrodes in a first direction for a period of time, then applying a field between a second set of electrodes in a second direction for a period of time, then repeating that cycle for an extended duration (e.g., over a period of days, weeks, or months). In order to generate the TTFields, current is applied to each electrode of the transducer array.

SUMMARY OF THE DISCLOSURE

The ceramic disks used in the conventional system have a rough surface, and so, too, does the patient's skin, which means the disks cannot be attached directly on the skin without the hydrogel due to an imperfect contact area. The use of hydrogel has a number of drawbacks, including the problem of the hydrogel drying out and cracking (which would also form an imperfect contact area), conductive properties that vary according to the moisture content in the hydrogel (which varies over time), and the need for moisture/humidity-controlled packaging for the hydrogel prior to use. Moreover, some patients suffer from skin irritation from the hydrogel. Additionally, some patients may suffer from skin irritation where an adhesive is used as a skin contact layer. What is needed is a skin contact layer between the device and the skin that does not require the use of hydrogel. In some cases, there is a need for a skin contact layer between the device and the skin that does not require the use of either hydrogel or an adhesive as a skin contact layer. The present invention by-passes the need for ceramic disks and a hydrogel layer or an adhesive layer and instead utilizes a non-hydrogel skin-interface material that can replace both components.

In one aspect, the present disclosure describes a method, comprising: applying a non-hydrogel skin-interface material to a patient's skin, the non-hydrogel skin-interface material being configured to contact the patient's skin and to conform to contours and/or irregularities of the patient's skin; and applying an electrode assembly to a surface of the non-hydrogel skin-interface material.

In another aspect, the present disclosure describes a transducer array, comprising: an electrode layer comprising one or more electrode; and a non-hydrogel skin-interface material for placement between a surface of the electrode layer and a patient's skin, the non-hydrogel skin-interface material being configured to contact the patient's skin and to conform to contours and/or irregularities of the patient's skin.

In embodiments described herein, the non-hydrogel skin-interface material can be a non-hydrogel adhesive-free skin-interface material.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
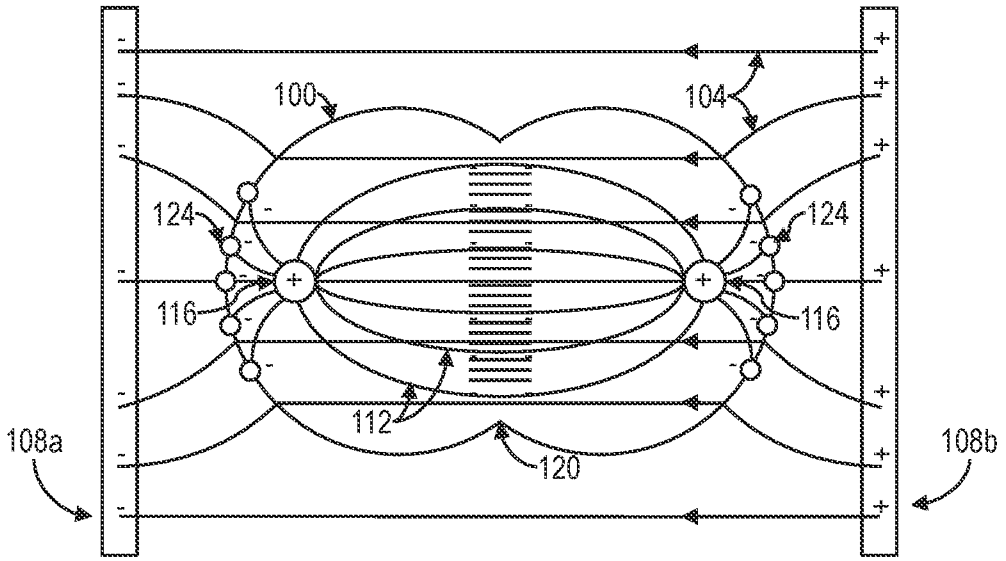
FIG. 1 is a schematic diagram of exemplary electrodes as applied to a field target such as living tissue.

Before explaining at least one implementation of the inventive concept(s) in detail by way of exemplary language and results, it is to be understood that the inventive concept (s) is not limited in its application to the details of construction and the arrangement of the components set forth in the following description. The inventive concept(s) is capable of other implementations or of being practiced or carried out in various ways. As such, the language used herein is intended to be given the broadest possible scope and meaning; and the implementations are meant to be exemplary—not exhaustive. Also, it is to be understood that the phraseology and terminology employed herein is for the purpose of description and should not be regarded as limiting.

Headings are provided for convenience only and are not to be construed to limit the invention in any manner. Implementations illustrated under any heading or in any portion of the disclosure may be combined with implementations illustrated under the same or any other heading or other portion of the disclosure. Any combination of the elements described herein in all possible variations thereof is encompassed by the invention unless otherwise indicated herein or otherwise clearly contradicted by context.

Unless otherwise required by context, singular terms shall include pluralities and plural terms shall include the singular, with the exception that the term "plurality" as used herein, does not include the singular.

All patents or published patent applications referenced in any portion of this application are herein expressly incorporated by reference in their entirety to the same extent as if each individual patent or publication was specifically and individually indicated to be incorporated by reference.

All of the assemblies, systems, kits, and/or methods disclosed herein can be made and executed without undue experimentation in light of the present disclosure. Where a method claim does not specifically state in the claims or description that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of implementations described in the specification.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." The term "plurality" refers to "two or more."

The use of the term "at least one" will be understood to include one as well as any quantity more than one. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive.

The term "patient" as used herein includes human and veterinary subjects. It also includes mammals, where "mammal" for purposes of treatment refers to any animal classified as a mammal, including (but not limited to) humans, domestic and farm animals, nonhuman primates, and any other animal that has mammary tissue.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

As used herein, the term "TTField" (TTFields, or TTF(s)) means tumor treating field. TTFields are low intensity (e.g., 1-10 V/cm, such as, for example, 1-4 V/cm) alternating electric fields of medium frequencies (about 50 kHz-1 MHZ, and more preferably from about 150 kHz-500 kHz) that when applied to a conductive medium, such as a human body, via electrodes, may be used, for example, to treat tumors as described in U.S. Pat. Nos. 7,016,725, 7,089,054, 7,333,852, 7,565,205, 7,805,201, and 8,244,345 by Palti (each of which is incorporated herein by reference) and in a publication by Kirson (see Eilon D. Kirson, et al., "Disruption of Cancer Cell Replication by Alternating Electric Fields", Cancer Res. 2004 64:3288-3295). TTFields have been shown to have the capability to specifically affect cancer cells and serve, among other uses, for treating cancer. TTFields therapy is an approved mono-treatment for recurrent glioblastoma (GBM), and an approved combination therapy with chemotherapy for newly diagnosed GBM patients.

As used herein, the term TTSignal(s) is an electrical signal that, when received by electrodes applied to a conductive medium, such as a human body, causes the electrodes to generate the TTField described above. The TT Signal is often an AC electrical signal having an alternating current waveform.

The term "transducer array", as used herein, may mean a conductive transducer array or a non-conductive transducer array. Exemplary transducer arrays may include, for example, transducer arrays disclosed in any one of U.S. Patent Publication No. 2021/0346693 entitled "CONDUCTIVE PAD GENERATING TUMOR TREATING FIELD AND METHODS OF PRODUCTION AND USE THEREOF" and U.S. Patent Publication No. 2022/0193404 A1 entitled "OPTIMIZATION OF COMPOSITE ELECTRODE" each of which are hereby incorporated herein in their entirety.

Referring now to the drawings and in particular to FIG. 1, shown therein is a diagram of an exemplary implementation of a field target 100 (i.e., a dividing cell), under the influence of external TTFields, generally indicated as lines 104, generated by a first electrode 108*a* having a negative charge and a second electrode 108*b* having a positive charge. Further shown are microtubules 112 that are known to have a very strong dipole moment. This strong polarization makes the microtubules 112, as well as other polar macromolecules and especially those that have a specific orientation within the field target 100 or its surroundings, susceptible to electric fields. The positive charges of the microtubules 112 are located at two centrioles 116 while two sets of negative poles are at a center 120 of the field target 100 and point of attachment 124 of the microtubules 112 to the cell membrane. The locations of the charges form sets of double dipoles and therefore are susceptible to electric fields of differing directions.

Figure 2:
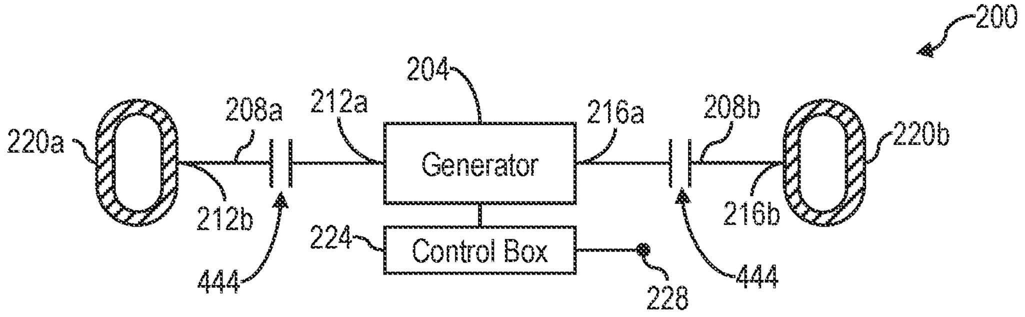
FIG. 2 is a schematic diagram of an exemplary electronic device configured to generate a TTField.

Referring now to FIG. 2, the TTFields described above that have been found to advantageously destroy tumor cells may be generated by an electronic apparatus 200. FIG. 2 is a simple schematic diagram of the electronic apparatus 200 illustrating major components thereof. The electronic apparatus 200 includes an electric field generator 204 and a pair of conductive leads 208, including first conductive lead 208*a* and second conductive lead 208*b*. The first conductive lead 208*a* includes a first end 212*a* and a second end 212*b*. The second conductive lead 208*b* includes a first end 216*a* and a second end 216*b*. The first end 212*a* of the first conductive lead 208*a* is conductively attached to the electric field generator 204 and the first end 216*a* of the second conductive lead 208*b* is conductively attached to the electric field generator 204.

The electronic apparatus 200 may also be provided with a first transducer array 220*a* and a second transducer array 220*b*. The electric field generator 204 generates desirable electric signals (TTSignals) in the shape of waveforms or trains of pulses as an output. The second end 212*b* of the first conductive lead 208*a* is connected to a first transducer array 220*a* and the second end 216*b* of the second conductive lead 208*b* is connected to a second transducer array 220*b*, that is supplied with the electric signals (e.g., wave forms).

Each of the first transducer array 220*a* and the second transducer array 220*b* are in contact with, or otherwise associated with, a field target 100 (see FIG. 1) such as living tissue (e.g., a patient) or a phantom made of material(s) having similar conductive properties as living tissue). The electric signals generate an electric field (i.e., TTField) that may be capacitively coupled into the field target 100, the TTField having a frequency and an amplitude, to be generated between the first transducer array 220*a* and the second transducer array 220*b* in the field target 100.

Each of the first transducer array 220*a* and the second transducer array 220*b* include one or more conductive electrode 300 (shown in FIG. 3) that may be capacitively coupled with the field target 100 by a non-conductive layer. Alternative constructions for the first transducer array 220*a* and the second transducer array 220*b* may also be used, including, for example, transducer arrays using a non-conductive layer formed of a ceramic element that is disc shaped, or is not disc-shaped, and/or non-conductive layer(s) that use non-ceramic dielectric materials positioned over a plurality of flat conductors. Examples of the latter include polymer films disposed over electrical contacts on a printed circuit board or over flat pieces of metal.

In some implementations, the first transducer array 220*a* and the second transducer array 220*b* may also include electrodes 300 (shown in FIG. 3) that are not capacitively coupled with the field target 100. In this situation, each of the first transducer array 220*a* and the second transducer array 220*b* may be implemented using a region of a conductive material that is configured for placement against a person's body, with no insulating dielectric layer disposed between the conductive elements and the body. Examples of the conductive material include, but are not limited to, a conductive film, a conductive fabric, and/or a conductive foam. Other alternative constructions for implementing the first transducer array 220*a* and the second transducer array 220*b* may also be used, as long as they are capable of delivering TTFields to the field target 100.

While the electronic apparatus 200 shown in FIG. 2 comprises only two transducer arrays 220 (the first transducer array 220*a* and the second transducer array 220*b*), yet, in some implementations, the electronic apparatus 200 may comprise more than two transducer arrays 220.

The electric field generator 204 generates an alternating current waveform at frequencies in the range from about 50 kHz to about 1 MHz (for example, from about 100 kHz to about 200 kHz, or from about 100 kHz to about 120 kHz) (i.e., the TTFields). The required voltages are such that an electric field intensity in tissue within the treatment area is in the range of about 0.1 V/cm to about 100 V/cm, such as, for example, 1-4 V/cm. To achieve this field, the potential difference between two conductors (not shown) of the first transducer array 220*a* and the second transducer array 220*b* is determined by the relative impedances of the system components, i.e., a fraction of the electric field on each component is given by that component's impedance divided by a total circuit impedance.

In order to optimize the electric field (i.e., TTField) distribution, the first transducer array 220*a* and the second transducer array 220*b* (pair of transducer arrays 220) may be configured or oriented differently depending upon the application in which the pair of transducer arrays 220 are to be used. The pair of transducer arrays 220, as described herein, are externally applied to the field target 100. When the field target 100 is a patient, the pair of transducer arrays 220 may be applied to the patient's skin, in order to apply the electric current, and electric field (TTField), thereby generating current within the patient's tissue. Generally, the pair of transducer arrays 220 are placed on the patient's skin by a user (or helper) such that the electric field is generated across patient tissue within a treatment area. TTFields that are applied externally can be of a local type or widely distributed type, for example, the treatment of skin tumors and treatment of lesions close to the skin surface, or a tumor further in the body.

In one implementation, the user may be a medical professional, such as a doctor, nurse, therapist, or other person acting under the instruction of a doctor, nurse, or therapist. In another implementation, the user may be the patient, that is, the patient (and/or a helper) may place the pair of transducer arrays 220 on their treatment area.

Optionally and according to another exemplary implementation, the electronic apparatus 200 includes a control box 224 and a temperature sensor 228 coupled to the control box 224, which are included to control the amplitude of the electric field so as not to generate excessive heating in the treatment area.

When the control box 224 is included, the control box 224 controls the output of the electric field generator 204, for example, causing the output to remain constant at a value preset by the user. Alternatively, the control box 224 sets the output at the maximal value that does not cause excessive heating of the treatment area. In either of the above cases, the control box 224 may issue a warning, or the like, when a temperature of the treatment area (as sensed by temperature sensor 228) exceeds a preset limit. The temperature sensor 228 may be mechanically connected to and/or otherwise associated with the first transducer array 220*a* or the second transducer array 220*b*, or both, so as to sense the temperature of the field target 100 at either one or both of the first transducer array 220*a* or the second transducer array 220*b*.

In one implementation, the control box 224 may turn off, or decrease power of the TTSignal generated by the electrical field generator 204, if a temperature sensed by the temperature sensor 228 meets or exceeds a comfortability threshold. In one implementation, the comfortability threshold is the temperature at which a patient would be made uncomfortable while using the transducer arrays 220. In one implementation, the comfortability threshold is a temperature at or about 40 degrees Celsius. In one implementation, the comfortability threshold is a temperature of between about 39 degrees Celsius and 42 degrees Celsius, or a specific selected temperature between about 39 degrees Celsius and 42 degrees Celsius, such as, for example, 41 degrees Celsius.

The conductive leads 208 are standard isolated conductors with a flexible metal shield, preferably grounded thereby preventing spread of any electric field generated by the conductive leads 208. The transducer arrays 220 may have specific shapes and positioning so as to generate the TTField of a desired configuration, direction, and intensity at the treatment area and only at the treatment area so as to focus the treatment.

The specifications of the electronic apparatus 200 as a whole and its individual components are largely influenced by the fact that at the frequency of the TTFields living systems behave according to their "Ohmic", rather than their dielectric properties.

Figure 3:
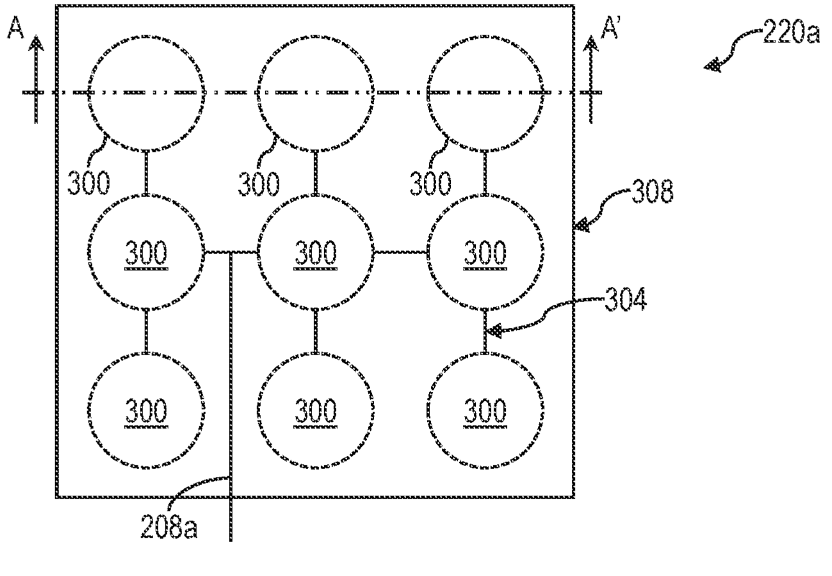
FIG. 3 is a schematic diagram of an exemplary transducer array.

Referring now to FIG. 3, shown therein is a diagram of an exemplary implementation of the first transducer array 220*a* constructed in accordance with the present disclosure. The second transducer array 220*b* may be similar in construction and function as the first transducer array 220*a*. For this reason, only the first transducer array 220*a* will be described herein for purposes of brevity. As will be described in greater detail below, the first transducer array 220*a* includes one or more electrode 300. As shown in FIG. 3, the first transducer array 220*a* is configured as a set of one or more electrode 300. The first transducer array 220*a* may utilize electrodes 300 that are configured to be capacitively coupled with the patient. In the example shown in FIG. 3, the first transducer array 220*a* is configured as multiple electrodes 300 (with each electrode 300, for example, being about 2 cm in diameter) that are interconnected via flex wires 304. Each electrode 300 may include a ceramic disk and a conductive electrode layer. In one implementation, the first transducer array 220*a* includes an outer peripheral edge 308.

Alternative constructions for the first transducer array 220*a* may be used, including, for example ceramic elements that are disc-shaped, ceramic elements that are not disc-shaped, and non-ceramic dielectric materials positioned over a plurality of flat conductors between the conductive electrode layer and a skin-facing surface of the first transducer array 220*a*. Examples of non-ceramic dielectric materials positioned over a plurality of flat conductors include: polymer films disposed over electrodes on a printed circuit board or over flat pieces of metal.

In one implementation, the first transducer array 220*a* may utilize electrodes 300 that are not capacitively coupled. In this situation, each electrode 300 of the first transducer array 220*a* would be implemented using a region of a conductive material that is configured for placement against a person's body, with no insulating dielectric layer disposed between the electrodes 300 and the body. Examples of the conductive material include a conductive film, a conductive fabric, and a conductive foam. Other alternative constructions for implementing the first transducer array 220*a* may also be used, as long as they are capable of delivering TTFields to the person's body.

In one implementation, the transducer arrays 220 may be constructed in accordance with any transducer array or pad disclosed in U.S. application Ser. No. 17/813,837 filed Jul. 20, 2022 entitled "CONDUCTIVE PAD GENERATING TUMOR TREATING FIELD AND METHODS OF PRODUCTION AND USE THEREOF", the entire contents of which are hereby incorporated herein in their entirety.

Figure 4A:
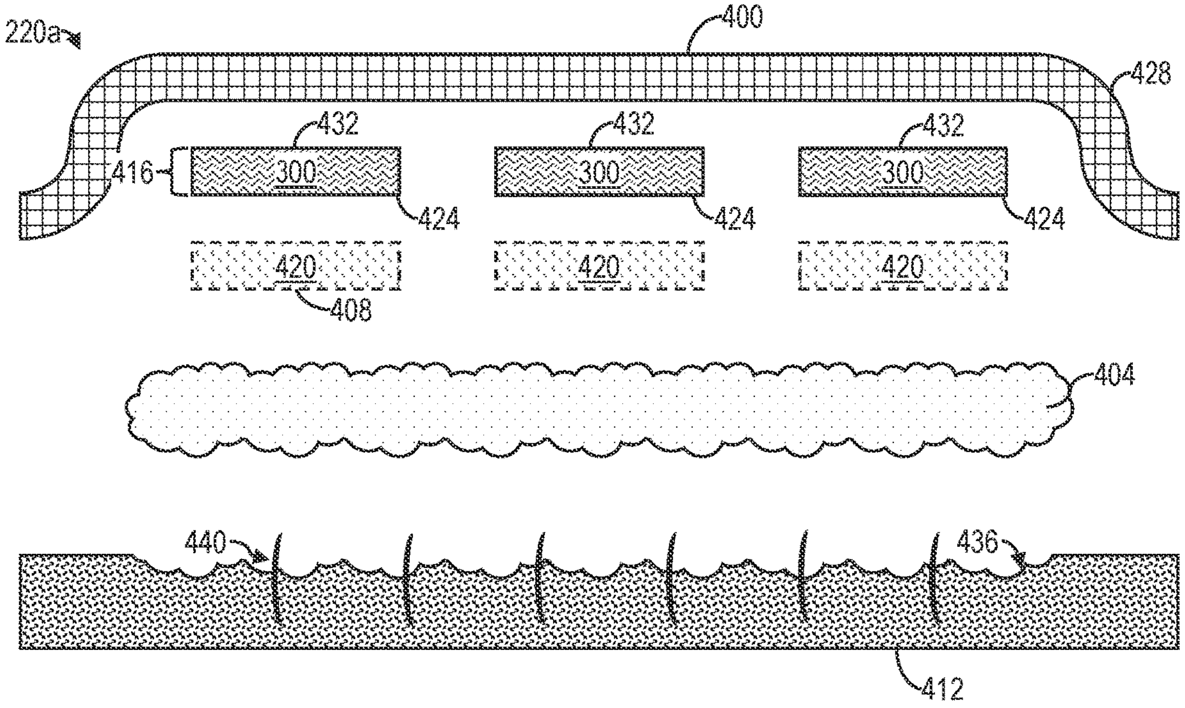
FIG. 4A is an exploded cross-sectional view of the transducer array shown in FIG. 3, taken along the line A-A' and looking in the direction of the arrows (shown in relation to the patient's skin)
Figure 4B:
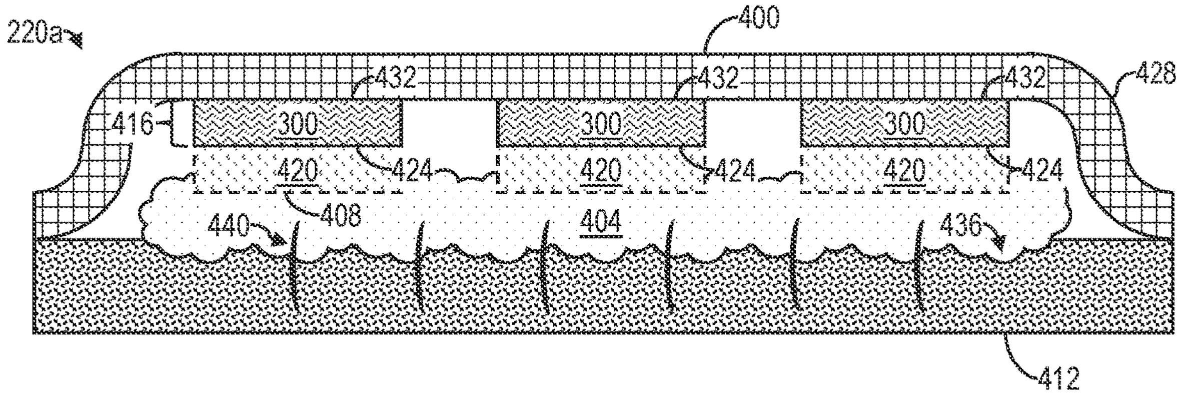
FIG. 4B is an assembled cross-sectional view of the transducer array shown in FIG. 4A.

Referring now to FIGS. 4A and 4B, shown therein is a cross-sectional view of a portion of the first transducer array 220*a* shown in FIG. 3, taken along the line A-A' and looking in the direction (and in the plane) of the arrows. FIG. 4A presents an exploded cross-sectional view of the portion of the first transducer array 220*a* (shown in relation to the patient's skin 412), while FIG. 4B presents an assembled cross-sectional view of the portion of the first transducer array 220*a* (again, shown in relation to the patient's skin 412). As shown in FIGS. 4A and 4B, the first transducer array 220*a* may comprise an electrode assembly 400 and a non-hydrogel skin-interface material 404 for placement between a skin facing surface 408 of the electrode assembly 400 and a patient's skin 412. In embodiments described herein, the non-hydrogel skin-interface material can be a non-hydrogel adhesive-free skin-interface material. The electrode assembly 400 may comprise an electrode layer 416 comprising one or more electrode 300 and, optionally, an intermediate layer 420 disposed on a skin facing surface 424 of the electrode layer 416. The intermediate layer 420 can be constructed of a dielectric material (e.g., ceramic, polymer, or the like) or a conductive material. The electrode assembly 400 may further comprise a covering layer 428 disposed on an outwardly facing surface 432 of the electrode layer 416.

The non-hydrogel skin-interface material 404 may be configured to contact the patient's skin and to conform to contours and/or irregularities 436 of the patient's skin 412. The contours and/or irregularities 436 of the patient's skin 412 may comprise at least one of a protrusion, an impression, a ridge, or a valley. In some implementations, the non-hydrogel skin-interface material 404 is optionally configured to encapsulate at least a portion of hairs 440 extending from the patient's skin 412.

In some embodiments, the non-hydrogel skin-interface material 404 helps to adhere/affix the first transducer array 220*a* and the second transducer array 220*b* to the patient's skin 412, provides a conductive pathway for the electric fields to pass between the one or more electrode 300 and the field target 100 (FIG. 1) through an intervening non-conductive or conductive layer, and is biocompatible.

In some implementations, the non-hydrogel skin-interface material 404 may be applied to the patient's skin 412 as a liquid non-hydrogel skin-interface material 404. In some implementations, the non-hydrogel skin-interface material 404 may be applied to the patient's skin 412 as a non-hydrogel adhesive-free skin-interface material, such as a dielectric grease suspension. The liquid non-hydrogel skin-interface material 404 may be sprayed onto the patient's skin 412 (i.e., the treatment area). Upon being applied, the liquid non-hydrogel skin-interface material 404 may be configured to convert into a non-liquid form. More specifically, the liquid non-hydrogel skin-interface material 404 may be configured to convert into a non-liquid form, i.e., solid form, without applying ultraviolet radiation. That is, the liquid non-hydrogel skin-interface material 404 may be configured to convert into a non-liquid form, i.e., solid form, after waiting a sufficient period of time.

In some implementations, the non-hydrogel skin-interface material 404 is a viscoelastic material. In some implementations, the non-hydrogel skin-interface material 404 comprises a silicone polymer. In such implementations, the silicone polymer, optionally, may be crosslinked. In some implementations, the non-hydrogel skin-interface material 404 is or comprises polydimethylsiloxane (PDMS), which, optionally, may be crosslinked.

In some implementations, the non-hydrogel skin-interface material 404 is a non-hydrogel adhesive-free skin-interface material, such as a dielectric material. In some such implementations, the non-hydrogel skin-interface material 404 is or comprises a dielectric (or silicone) grease. In some such implementations, the dielectric (or silicone) grease comprises a polydimethylsiloxane (PDMS) polymer, which, optionally, may be crosslinked.

In some implementations, the non-hydrogel skin-interface material 404 may be configured for placement between the electrode assembly 400 and the patient's skin 412 such that the skin facing surface 408 of the intermediate layer 420, e.g., at least a portion of the intermediate layer 420, is in contact with at least a portion of the non-hydrogel skin-interface material 404.

In some implementations, the non-hydrogel skin-interface material 404 is a conductive material. In some such implementations, the electrode assembly 400 further comprises one or more DC blocking capacitor 444 (see FIG. 2) in series with the one or more electrode 300 to prevent DC signals from reaching the first transducer array 220*a* or the second transducer array 220*b* (FIG. 2). In other implementations, the non-hydrogel skin-interface material 404 is a nonconductive material with a conductive material suspended therein. For example, the non-hydrogel skin-interface material 404 may be a skin mask (e.g., a cosmetic facial mask) comprising conductive particles. Conductive particles may include, but are not limited to, metal particles such as gold, silver or copper particles, and the like; or carbon particles, such as, for example, carbon flakes, carbon granules, carbon fibers, carbon nanotubes, single-walled carbon nanotubes, multi-walled carbon nanotubes, carbon black powder, graphite powder, carbon nanowires, carbon microcoils, and the like.

It will be understood by persons having ordinary skill in the art that the one or more DC blocking capacitor 444 may be a component of the electric field generator 204, either of the pair of conductive leads 208 (i.e., the first conductive lead 208*a* and/or the second conductive lead 208*b*) (as shown in FIG. 2), and/or any of the transducer arrays 220 (i.e., the first transducer array 220*a*, the second transducer array 220*b*, etc.).

The covering layer 428 may extend laterally beyond at least a portion of a perimeter of the electrode layer 416. More specifically, the covering layer 428 may extend laterally beyond at least a portion of a perimeter of the electrode layer 416 and may extend laterally beyond at least a portion of the outer peripheral edge 308 (FIG. 3) of the transducer array 220*a* such that at least a portion of the covering layer 428 is in contact with the non-hydrogel skin-interface material 404 and/or the patient's skin 412. In some implementations, for example, when the non-hydrogel skin-interface material 404 is a non-hydrogel adhesive-free skin-interface material, the covering layer 428 is an adhesive tape or bandage that operates to secure the electrode layer 416 to the patient's skin 412.

Figure 5:
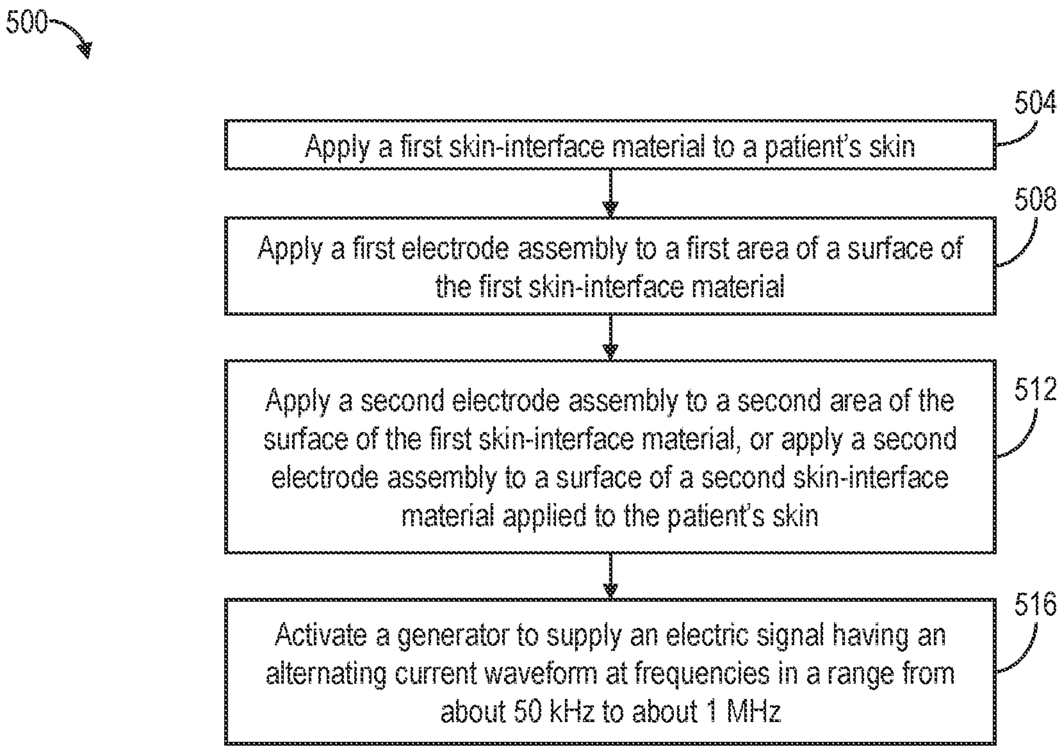
FIG. 5 is a process flow diagram of an exemplary method of using transducer arrays to apply TTFields to a patient.

Referring now to FIG. 5, shown therein is an exemplary method 500 of using the transducer arrays 220 to apply TTFields to a patient, the exemplary method 500 generally comprising the steps of: applying a first non-hydrogel skin-interface material 404 to a patient's skin 412 (step 504); applying a first electrode assembly 400 to a first area of a surface of the first non-hydrogel skin-interface material 404 (step 508); applying a second electrode assembly 400 to a second area of the surface of the first non-hydrogel skin-interface material 404, or applying the second electrode assembly 400 to a surface of a second non-hydrogel skin-interface material 404 applied to the patient's skin 412 (the second non-hydrogel skin-interface material 404 preferably being separate from the first non-hydrogel skin-interface material 404) (step 512); and activating a generator (i.e., the electric field generator 204) to supply an electric signal having an alternating current waveform at frequencies in a range from about 50 kHz to about 1 MHz (step 516) to the first electrode assembly 400 and the second electrode assembly 400.

The first non-hydrogel skin-interface material 404 may be configured to contact the patient's skin and to conform to contours and/or irregularities 436 in the patient's skin 412. In some implementations, the step of applying the first non-hydrogel skin-interface material 404 to the patient's skin 412 (step 504) is further defined as applying a first non-hydrogel skin-interface material 404 to the first area of the surface of the first non-hydrogel skin-interface material 404. In some implementations, the first non-hydrogel skin-interface material 404 may be applied to the patient's skin 412 as a first liquid non-hydrogel skin-interface material 404. Alternatively, the first non-hydrogel skin-interface material 404 may be applied to the patient's skin 412 as a grease suspension.

In some implementations, the step of applying the first non-hydrogel skin-interface material 404 to the patient's skin 412 (step 504) is further defined as spraying the first non-hydrogel skin-interface material 404 onto the patient's skin 412. Upon being applied, the first liquid non-hydrogel skin-interface material 404 may be configured to convert into a non-liquid form, i.e., a solid form. In some embodiments, the first liquid non-hydrogel skin-interface material 404 may be configured to convert into a non-liquid form without applying ultraviolet radiation. That is, the first liquid non-hydrogel skin-interface material 404 may be configured to convert into a non-liquid form, i.e., solid form, after waiting a sufficient period of time.

In some implementations, the step of applying the first electrode assembly 400 to the first area of the surface of the first non-hydrogel skin-interface material 404 (step 508) is further defined as: waiting a sufficient period of time for the first liquid non-hydrogel skin-interface material 404 to convert into a non-liquid form; and applying the first electrode assembly 400 to the first area of the surface of the first non-hydrogel skin-interface material 404 in the non-liquid form. The first electrode assembly 400 may comprise an electrode layer 416 comprising one or more electrode 300. The first electrode assembly 400 may further comprise a covering layer 428 extending laterally beyond at least a portion of a perimeter of the electrode layer 416 and may extend laterally beyond at least a portion of the outer peripheral edge 308 of the transducer array 220*a*.

In some implementations, the step of applying the first electrode assembly 400 to the first area of the surface of the first non-hydrogel skin-interface material 404 (step 508) is further defined as applying the first electrode assembly 400 to the first area of the surface of the first non-hydrogel skin-interface material 404 such that at least a portion of the covering layer 428 is in contact with the first non-hydrogel skin-interface material 404 or the patient's skin 412. The at least a portion of the covering layer 428 may have a bonding material, e.g., an adhesive layer, (not shown) on at least a portion of a skin-facing surface (not shown) of the covering layer 428 to aid in securing the first electrode assembly 400 to the patient's skin 412. The covering layer 428 may be an adhesive tape or bandage.

In some implementations, the first non-hydrogel skin-interface material 404 is a dielectric material. In such embodiments, the first electrode assembly 400 may further comprise the intermediate layer 420, which is a conductive material, and the step of applying the first electrode assembly 400 to the first area of the surface of the first non-hydrogel skin-interface material 404 (step 508) is further defined as applying the first electrode assembly 400 to the first area of the surface of the first non-hydrogel skin-interface material 404 such that at least a portion of the intermediate layer 420 is in contact with at least a portion of the first non-hydrogel skin-interface material 404.

In some implementations, the first non-hydrogel skin-interface material 404 is a viscoelastic material. In some implementations, the first non-hydrogel skin-interface material 404 comprises a silicone polymer. In such implementations, the silicone polymer, optionally, may be crosslinked. In some implementations, the first non-hydrogel skin-interface material 404 is or comprises polydimethylsiloxane (PDMS), which, optionally, may be crosslinked.

In some implementations, the first non-hydrogel skin-interface material 404 is a dielectric material. In some implementations, the non-hydrogel skin-interface material 404 is or comprises a dielectric (or silicone) grease. In some implementations, the dielectric (or silicone) grease comprises a polydimethylsiloxane (PDMS) polymer, which, optionally, may be crosslinked.

In some implementations, the first non-hydrogel skin-interface material 404 is a conductor. In some implementations, the step of applying the first electrode assembly 400 to the first area of the surface of the first non-hydrogel skin-interface material 404 (step 508) is further defined as applying the first electrode assembly 400 to the first area of the surface of the first non-hydrogel skin-interface material 404 such that at least a portion of the electrode layer 416 is electrically coupled with at least a portion of the first non-hydrogel skin-interface material 404. In some implementations, the first electrode assembly 400 may further comprise a DC blocking capacitor 444 in series with the one or more electrode 300. In some implementations, the first non-hydrogel skin-interface material 404 is a skin mask (e.g., a cosmetic facial mask) comprising conductive particles (for example, metal particles, or carbon particles).

The second non-hydrogel skin-interface material 404 may be configured to contact the patient's skin and to conform to contours and/or irregularities 436 in the patient's skin 412. In some implementations, the second non-hydrogel skin-interface material 404 may be applied to the patient's skin 412 as a second liquid non-hydrogel skin-interface material 404. Alternatively, the second non-hydrogel skin-interface material 404 may be applied to the patient's skin 412 as a grease suspension.

Upon being applied, the second liquid non-hydrogel skin-interface material 404 may be configured to convert into a non-liquid form, i.e., solid form. More specifically, the second liquid non-hydrogel skin-interface material 404 may be configured to convert into a non-liquid form without applying ultraviolet radiation. That is, the second liquid non-hydrogel skin-interface material 404 may be configured to convert into a non-liquid form after waiting a sufficient period of time.

In some implementations, the step of applying the second electrode assembly 400 to the second area of the surface of the first non-hydrogel skin-interface material 404, or applying the second electrode assembly 400 to the surface of the second non-hydrogel skin-interface material 404 applied to the patient's skin 412 (step 512) is further defined as: waiting a sufficient period of time for at least one of the first liquid non-hydrogel skin-interface material 404 and the second liquid non-hydrogel skin-interface material 404 to convert into a non-liquid form; and applying the second electrode assembly 400 to the second area of the surface of the first non-hydrogel skin-interface material 404, or applying the second electrode assembly 400 to the surface of the second non-hydrogel skin-interface material 404. The second electrode assembly 400 may comprise an electrode layer 416 comprising one or more electrode 300. The second electrode assembly 400 may further comprise the covering layer 428 extending laterally beyond at least a portion of a perimeter of the electrode layer 416 and may extend laterally beyond at least a portion of the outer peripheral edge 308 of the transducer array 220*a*.

In some implementations, the step of applying the second electrode assembly 400 to the second area of the surface of the first non-hydrogel skin-interface material 404, or applying the second electrode assembly 400 to the surface of the second non-hydrogel skin-interface material 404 applied to the patient's skin 412 (step 512) is further defined as applying the second electrode assembly 400 to the second area of the surface of the first non-hydrogel skin-interface material 404 such that at least a portion of the covering layer 428 is in contact with the first non-hydrogel skin-interface material 404 or the patient's skin 412, or applying the second electrode assembly 400 to the surface of the second non-hydrogel skin-interface material 404 applied to the patient's skin 412 such that at least a portion of the covering layer 428 is in contact with the second non-hydrogel skin-interface material 404 or the patient's skin 412. The at least a portion of the covering layer 428 may have an adhesive layer (not shown) on at least a portion of a skin-facing surface (not shown) of the covering layer 428 to aid in securing the second electrode assembly 400 to the patient's skin 412. The covering layer 428 may be an adhesive tape or bandage.

In some implementations, the second non-hydrogel skin-interface material 404 is a dielectric material. In some embodiments, the second electrode assembly 400 may further comprise the intermediate layer 420, and the step of applying the second electrode assembly 400 to the second area of the surface of the first non-hydrogel skin-interface material 404, or applying the second electrode assembly 400 to the surface of the second non-hydrogel skin-interface material 404 applied to the patient's skin 412 (step 512) is further defined as applying the second electrode assembly 400 to the second area of the surface of the first non-hydrogel skin-interface material 404 such that at least a portion of the intermediate layer 420 is in contact with at least a portion of the first non-hydrogel skin-interface material 404, or applying the second electrode assembly 400 to the surface of the second non-hydrogel skin-interface material 404 applied to the patient's skin 412 such that at least a portion of the intermediate layer 420 is in contact with at least a portion of the second non-hydrogel skin-interface material 404.

In some implementations, the second non-hydrogel skin-interface material 404 is a viscoelastic material. In some implementations, the second non-hydrogel skin-interface material 404 comprises a silicone polymer. In such implementations, the silicone polymer, optionally, may be crosslinked. In some implementations, the second non-hydrogel skin-interface material 404 is or comprises polydimethylsiloxane (PDMS), which, optionally, may be crosslinked.

In some implementations, the second non-hydrogel skin-interface material 404 is a dielectric material. In some implementations, the second non-hydrogel skin-interface material 404 is or comprises a dielectric (or silicone) grease. In some implementations, the dielectric (or silicone) grease comprises a polydimethylsiloxane (PDMS) polymer, which, optionally, may be crosslinked.

In some implementations, the second non-hydrogel skin-interface material 404 is a conductor. In some implementations, the step of applying the second electrode assembly 400 to the second area of the surface of the first non-hydrogel skin-interface material 404, or applying the second electrode assembly 400 to the surface of the second non-hydrogel skin-interface material 404 applied to the patient's skin 412 (step 512) is further defined as applying the second electrode assembly 400 to the second area of the surface of the first non-hydrogel skin-interface material 404 such that at least a portion of the electrode layer 416 is electrically coupled with at least a portion of the first non-hydrogel skin-interface material 404, or applying the second electrode assembly 400 to the surface of the second non-hydrogel skin-interface material 404 applied to the patient's skin 412 such that at least a portion of the electrode layer 416 is electrically coupled with at least a portion of the second non-hydrogel skin-interface material 404. In some implementations, the second electrode assembly 400 may further comprise a DC blocking capacitor 444 in series with the one or more electrode 300. In some implementations, the second non-hydrogel skin-interface material 404 is a skin mask (e.g., a cosmetic facial mask) comprising conductive particles.

In some implementations, the step of activating the electric field generator 204 to supply the electric signal having an alternating current waveform at frequencies in a range from about 50 kHz to about 1 MHz (step 516) is further defined as activating the electric field generator 204 to supply the electric signal to the first electrode assembly 400 and the second electrode assembly 400, thereby generating an electric field (i.e., a TTField) for a period of time, wherein the electric signal has an alternating current waveform at frequencies in a range from about 50 kHz to about 1 MHz.

The following is a number list of non-limiting illustrative embodiments of the inventive concept disclosed herein:

1. A method, comprising:
applying a non-hydrogel skin-interface material to a patient's skin, the non-hydrogel skin-interface material being configured to contact the patient's skin and to conform to contours and/or irregularities of the patient's skin; and
applying an electrode assembly to a surface of the non-hydrogel skin-interface material.

2. The method of illustrative embodiment 1, wherein applying the electrode assembly to the surface of the non-hydrogel skin-interface material is defined further as applying the electrode assembly to the surface of the non-hydrogel skin-interface material such that an alternating current waveform may be applied to the patient via the non-hydrogel skin-interface material.

3. The method of illustrative embodiment 1, wherein the non-hydrogel skin-interface material is applied as a liquid non-hydrogel skin-interface material or a grease suspension.

4. The method of any one of illustrative embodiments 1-3, wherein the step of applying the non-hydrogel skin-interface material to the patient's skin is further defined as spraying the non-hydrogel skin-interface material onto the patient's skin.

5. The method of illustrative embodiment 1, wherein the step of applying the non-hydrogel skin-interface material to the patient's skin is further defined as applying a liquid non-hydrogel skin-interface material to the patient's skin, and the step of applying the electrode assembly to the surface of the non-hydrogel skin-interface material is further defined as:
waiting a sufficient period of time for the liquid non-hydrogel skin-interface material to convert into a non-liquid form; and
applying the electrode assembly to the surface of the non-hydrogel skin-interface material in the non-liquid form.

6. The method of illustrative embodiment 5, wherein the non-hydrogel skin-interface material is configured to convert into the non-liquid form without applying ultraviolet radiation, and wherein the step of applying the electrode assembly to a surface of the non-hydrogel skin-interface material includes waiting the sufficient period of time for the liquid non-hydrogel skin-interface material to convert into the non-liquid form before applying the electrode assembly to the surface of the non-hydrogel skin-interface material.

7. The method of any one of illustrative embodiments 1-6, wherein the electrode assembly comprises an electrode layer comprising one or more electrode and a covering layer disposed on an outwardly facing surface of the electrode layer, the covering layer extending laterally beyond at least a portion of a perimeter of the electrode layer, and the step of applying the electrode assembly to the surface of the non-hydrogel skin-interface material is further defined as applying the electrode assembly to the surface of the non-hydrogel skin-interface material such that at least a portion of the covering layer is in contact with the non-hydrogel skin-interface material or the patient's skin or both.

8. The method of illustrative embodiment 7, wherein the at least a portion of the covering layer in contact with the non-hydrogel skin-interface material or the patient's skin or both has an adhesive layer on at least a portion of a skin-facing surface of the covering layer to aid in securing the electrode assembly to the patient's skin.

9. The method of illustrative embodiment 7, wherein the covering layer is an adhesive tape or bandage.

10. The method of any one of illustrative embodiments 1-9, wherein the non-hydrogel skin-interface material is a dielectric, the electrode assembly comprises an electrode layer comprising one or more electrode and a conductive layer disposed on a skin facing surface of the electrode layer, and the step of applying the electrode assembly to the surface of the non-hydrogel skin-interface material is further defined as applying the electrode assembly to the surface of the non-hydrogel skin-interface material such that at least a portion of the conductive layer is in contact with at least a portion of the non-hydrogel skin-interface material.

11. The method of illustrative embodiment 10, wherein the non-hydrogel skin-interface material is or comprises a silicone polymer, which, optionally, may be crosslinked.

12. The method of illustrative embodiment 10, wherein the non-hydrogel skin-interface material is or comprises a polydimethylsiloxane polymer, which, optionally, may be crosslinked.

13. The method of illustrative embodiment 10, wherein the non-hydrogel skin-interface material is or comprises a dielectric grease.

14. The method of illustrative embodiment 13, wherein the dielectric grease comprises a polydimethylsiloxane polymer, which, optionally, may be crosslinked.

15. The method of illustrative embodiment 10, wherein the non-hydrogel skin-interface material is a viscoelastic material.

16. The method of any one of illustrative embodiments 1-15, wherein the electrode assembly is a first electrode assembly, the non-hydrogel skin-interface material is a first non-hydrogel skin-interface material, the step of applying the first electrode assembly to the surface of the first non-hydrogel skin-interface material is further defined as applying the first electrode assembly to a first area of the surface of the first non-hydrogel skin-interface material, and the method further comprises:

applying a second electrode assembly to a second area of the surface of the first non-hydrogel skin-interface material or applying the second electrode assembly to a surface of a second non-hydrogel skin-interface material applied to the patient's skin; and activating a generator to supply an electrical signal comprising an alternating current waveform to the first electrode assembly and the second electrode assembly, thereby generating an electric field within the patient for a period of time.

17. The method of illustrative embodiment 16, wherein the step of activating the generator is further defined as activating the generator to supply the electrical signal having an alternating current waveform at frequencies in a range from about 50 kHz to about 1 MHz.

18. The method of any one of illustrative embodiments 1-17, wherein the non-hydrogel skin-interface material is a conductor, the electrode assembly comprises an electrode layer comprising one or more electrode, and the step of applying the electrode assembly to the surface of the non-hydrogel skin-interface material is further defined as applying the electrode assembly to the surface of the non-hydrogel skin-interface material such that at least a portion of the electrode layer is electrically coupled with at least a portion of the non-hydrogel skin-interface material.

19. The method of illustrative embodiment 18, wherein the electrode assembly further comprises a DC blocking capacitor in series with the one or more electrode.

20. The method of illustrative embodiment 18, wherein the non-hydrogel skin-interface material is a skin mask comprising conductive particles.

21. The method of any one of illustrative embodiments 1-20, wherein the non-hydrogel skin-interface material is a non-hydrogel adhesive-free skin-interface material.

22. A transducer array, comprising:

an electrode assembly including an electrode layer comprising one or more electrode; and a non-hydrogel skin-interface material for placement between a surface of the electrode layer and a patient's skin, the non-hydrogel skin-interface material being configured to contact the patient's skin and to conform to contours and/or irregularities of the patient's skin.

23. The transducer array of illustrative embodiment 22, wherein the contours and/or irregularities comprises at least one of a protrusion, an impression, a ridge, or a valley.

24. The transducer array of any one of illustrative embodiments 22-23, wherein the non-hydrogel skin-interface material is a liquid non-hydrogel skin-interface material or a grease suspension.

25. The transducer array of illustrative embodiment 24, wherein the non-hydrogel skin-interface material is a liquid non-hydrogel skin-interface material configured to convert into a non-liquid form without applying ultraviolet radiation.

26. The transducer array of illustrative embodiment 22, wherein the non-hydrogel skin-interface material is a viscoelastic material.

27. The transducer array of illustrative embodiment 22, wherein the non-hydrogel skin-interface material is a dielectric material, and the electrode assembly further comprises a conductive material disposed between the surface of the electrode layer and the non-hydrogel skin-interface material.

28. The transducer array of illustrative embodiment 22, wherein the non-hydrogel skin-interface material comprises a silicone polymer, which, optionally, may be crosslinked.

29. The transducer array of illustrative embodiment 22, wherein the non-hydrogel skin-interface material is or comprises polydimethylsiloxane (PDMS), which, optionally, may be crosslinked.

30. The transducer array of illustrative embodiment 22, wherein the non-hydrogel skin-interface material is or comprises a dielectric grease.

31. The transducer array of illustrative embodiment 30, wherein the dielectric grease comprises polydimethylsiloxane (PDMS), which, optionally, may be crosslinked.

32. The transducer array of any one of illustrative embodiments 22-31, further comprising a covering layer disposed on an outwardly facing surface of the electrode layer, the covering layer extending laterally beyond at least a portion of a perimeter of the electrode layer such that at least a portion of the covering layer is in contact with the non-hydrogel skin-interface material or the patient's skin.

33. The transducer array of illustrative embodiment 32, wherein the covering layer is an adhesive tape or bandage.

34. The transducer array of any one of illustrative embodiments 22-33, wherein the non-hydrogel skin-interface material is a conductive material.

35. The transducer array of illustrative embodiment 34, wherein the electrode assembly further comprises a DC blocking capacitor in series with the one or more electrode.

36. The transducer array of any one of illustrative embodiments 22-33, wherein the non-hydrogel skin-interface material is a nonconductive material with a conductive material suspended therein.

37. The transducer array of illustrative embodiment 36, wherein the nonconductive material is a skin mask and the conductive material is conductive particles.

38. The transducer array of any one of illustrative embodiments 22-37, wherein the non-hydrogel skin-interface material is a non-hydrogel adhesive-free skin-interface material.

39. An electronic apparatus comprising:

an electric field generator comprising circuitry configured to generate an alternating current electrical signal having an alternating current waveform;

a first conducting lead connected to the electric field generator so as to receive the alternating current electrical signal;

a second conducting lead connected to the electric field generator so as to receive the alternating current electrical signal;

a first transducer array connected to the first conducting lead;

a second transducer array connected to the second conducting lead;

wherein the first transducer array comprises:

an electrode layer comprising one or more electrode; and a non-hydrogel skin-interface material for placement between a surface of the electrode layer and a patient's skin, the non-hydrogel skin-interface material being configured to contact the patient's skin and to conform to contours and/or irregularities of the patient's skin.

40. The electronic apparatus of illustrative embodiment 39, wherein the non-hydrogel skin-interface material is a conductive material, and further comprising a DC blocking capacitor in series with the first conducting lead.

41. The electronic apparatus of illustrative embodiment 40, wherein the DC blocking capacitor is a first DC blocking capacitor, and further comprising a second DC blocking capacitor in series with the second conducting lead.

42. The electronic apparatus of illustrative embodiment 39, wherein the non-hydrogel skin-interface material is a nonconductive material with a conductive material suspended therein.

43. The electronic apparatus of any one of illustrative embodiments 39-42, wherein the non-hydrogel skin-interface material is a non-hydrogel adhesive-free skin-interface material.

44. A method, comprising:

applying a non-hydrogel adhesive-free skin-interface material to a patient's skin, the non-hydrogel adhesive-free skin-interface material being configured to contact the patient's skin and to conform to contours and/or irregularities of the patient's skin; and applying an electrode assembly to a surface of the non-hydrogel adhesive-free skin-interface material.

45. The method of illustrative embodiment 44, wherein applying the electrode assembly to the surface of the non-hydrogel adhesive-free skin-interface material is defined further as applying the electrode assembly to the surface of the non-hydrogel adhesive-free skin-interface material such that an alternating current waveform may be applied to the patient via the non-hydrogel adhesive-free skin-interface material.

46. The method of illustrative embodiment 44, wherein the non-hydrogel adhesive-free skin-interface material is applied as a liquid non-hydrogel adhesive-free skin-interface material or a grease suspension.

47. The method of any one of illustrative embodiments 44-46, wherein the step of applying the non-hydrogel adhesive-free skin-interface material to the patient's skin is further defined as spraying the non-hydrogel adhesive-free skin-interface material onto the patient's skin.

48. The method of illustrative embodiment 44, wherein the step of applying the non-hydrogel adhesive-free skin-interface material to the patient's skin is further defined as applying a liquid non-hydrogel adhesive-free skin-interface material to the patient's skin, and the step of applying the electrode assembly to the surface of the non-hydrogel adhesive-free skin-interface material is further defined as:

waiting a sufficient period of time for the liquid non-hydrogel adhesive-free skin-interface material to convert into a non-liquid form; and applying the electrode assembly to the surface of the non-hydrogel adhesive-free skin-interface material in the non-liquid form.

49. The method of illustrative embodiment 48, wherein the non-hydrogel adhesive-free skin-interface material is configured to convert into the non-liquid form without applying ultraviolet radiation, and wherein the step of applying the electrode assembly to a surface of the non-hydrogel adhesive-free skin-interface material includes waiting the sufficient period of time for the liquid non-hydrogel adhesive-free skin-interface material to convert into the non-liquid form before applying the electrode assembly to the surface of the non-hydrogel adhesive-free skin-interface material.

50. The method of any one of illustrative embodiments 44-49, wherein the electrode assembly comprises an electrode layer comprising one or more electrode and a covering layer disposed on an outwardly facing surface of the electrode layer, the covering layer extending laterally beyond at least a portion of a perimeter of the electrode layer, and the step of applying the electrode assembly to the surface of the non-hydrogel adhesive-free skin-interface material is further defined as applying the electrode assembly to the surface of the non-hydrogel adhesive-free skin-interface material such that at least a portion of the covering layer is in contact with the non-hydrogel adhesive-free skin-interface material or the patient's skin or both.

51. The method of illustrative embodiment 50, wherein the at least a portion of the covering layer in contact with the non-hydrogel adhesive-free skin-interface material or the patient's skin or both has an adhesive layer on at least a portion of a skin-facing surface of the covering layer to aid in securing the electrode assembly to the patient's skin.

52. The method of illustrative embodiment 50, wherein the covering layer is an adhesive tape or bandage.

53. The method of any one of illustrative embodiments 44-52, wherein the non-hydrogel adhesive-free skin-interface material is a dielectric, the electrode assembly comprises an electrode layer comprising one or more electrode and a conductive layer disposed on a skin facing surface of the electrode layer, and the step of applying the electrode assembly to the surface of the non-hydrogel adhesive-free skin-interface material is further defined as applying the electrode assembly to the surface of the non-hydrogel adhesive-free skin-interface material such that at least a portion of the conductive layer is in contact with at least a portion of the non-hydrogel adhesive-free skin-interface material.

54. The method of illustrative embodiment 53, wherein the non-hydrogel adhesive-free skin-interface material is or comprises a silicone polymer, which, optionally, may be crosslinked.

55. The method of illustrative embodiment 53, wherein the non-hydrogel adhesive-free skin-interface material is or comprises a polydimethylsiloxane polymer, which, optionally, may be crosslinked.

56. The method of illustrative embodiment 53, wherein the non-hydrogel adhesive-free skin-interface material is or comprises a dielectric grease.

57. The method of illustrative embodiment 56, wherein the dielectric grease comprises a polydimethylsiloxane polymer, which, optionally, may be crosslinked.

58. The method of illustrative embodiment 53, wherein the non-hydrogel adhesive-free skin-interface material is a viscoelastic material.

59. The method of any one of illustrative embodiments 44-58, wherein the electrode assembly is a first electrode assembly, the non-hydrogel adhesive-free skin-interface material is a first non-hydrogel adhesive-free skin-interface material, the step of applying the first electrode assembly to the surface of the first non-hydrogel adhesive-free skin-interface material is further defined as applying the first electrode assembly to a first area of the surface of the first non-hydrogel adhesive-free skin-interface material, and the method further comprises:

applying a second electrode assembly to a second area of the surface of the first non-hydrogel adhesive-free skin-interface material or applying the second electrode assembly to a surface of a second non-hydrogel adhesive-free skin-interface material applied to the patient's skin; and activating a generator to supply an electrical signal comprising an alternating current waveform to the first electrode assembly and the second electrode assembly, thereby generating an electric field within the patient for a period of time.

60. The method of illustrative embodiment 59, wherein the step of activating the generator is further defined as activating the generator to supply the electrical signal having an alternating current waveform at frequencies in a range from about 50 kHz to about 1 MHz.

61. The method of any one of illustrative embodiments 44-60, wherein the non-hydrogel adhesive-free skin-interface material is a conductor, the electrode assembly comprises an electrode layer comprising one or more electrode, and the step of applying the electrode assembly to the surface of the non-hydrogel adhesive-free skin-interface material is further defined as applying the electrode assembly to the surface of the non-hydrogel adhesive-free skin-interface material such that at least a portion of the electrode layer is electrically coupled with at least a portion of the non-hydrogel adhesive-free skin-interface material.

62. The method of illustrative embodiment 61, wherein the electrode assembly further comprises a DC blocking capacitor in series with the one or more electrode.

63. The method of illustrative embodiment 61, wherein the non-hydrogel adhesive-free skin-interface material is a skin mask comprising conductive particles.

64. A transducer array, comprising:

an electrode assembly including an electrode layer comprising one or more electrode; and a non-hydrogel adhesive-free skin-interface material for placement between a surface of the electrode layer and a patient's skin, the non-hydrogel adhesive-free skin-interface material being configured to contact the patient's skin and to conform to contours and/or irregularities of the patient's skin.

65. The transducer array of illustrative embodiment 64, wherein the contours and/or irregularities comprises at least one of a protrusion, an impression, a ridge, or a valley.

66. The transducer array of illustrative embodiment 64 or 65, wherein the non-hydrogel adhesive-free skin-interface material is a liquid non-hydrogel adhesive-free skin-interface material or a grease suspension.

67. The transducer array of illustrative embodiment 66, wherein the non-hydrogel adhesive-free skin-interface material is a liquid non-hydrogel adhesive-free skin-interface material configured to convert into a non-liquid form without applying ultraviolet radiation.

68. The transducer array of illustrative embodiment 64, wherein the non-hydrogel adhesive-free skin-interface material is a viscoelastic material.

69. The transducer array of illustrative embodiment 64, wherein the non-hydrogel adhesive-free skin-interface material is a dielectric material, and the electrode assembly further comprises a conductive material disposed between the surface of the electrode layer and the non-hydrogel adhesive-free skin-interface material.

70. The transducer array of illustrative embodiment 64, wherein the non-hydrogel adhesive-free skin-interface material comprises a silicone polymer, which, optionally, may be crosslinked.

71. The transducer array of illustrative embodiment 64, wherein the non-hydrogel adhesive-free skin-interface material is or comprises polydimethylsiloxane (PDMS), which, optionally, may be crosslinked.

72. The transducer array of illustrative embodiment 64, wherein the non-hydrogel adhesive-free skin-interface material is or comprises a dielectric grease.

73. The transducer array of illustrative embodiment 72, wherein the dielectric grease comprises polydimethylsiloxane (PDMS), which, optionally, may be crosslinked.

74. The transducer array of any one of illustrative embodiments 64-73, further comprising a covering layer disposed on an outwardly facing surface of the electrode layer, the covering layer extending laterally beyond at least a portion of a perimeter of the electrode layer such that at least a portion of the covering layer is in contact with the non-hydrogel adhesive-free skin-interface material or the patient's skin.

75. The transducer array of illustrative embodiment 74, wherein the covering layer is an adhesive tape or bandage.

76. The transducer array of any one of illustrative embodiments 64-75, wherein the non-hydrogel adhesive-free skin-interface material is a conductive material.

77. The transducer array of illustrative embodiment 76, wherein the electrode assembly further comprises a DC blocking capacitor in series with the one or more electrode.

78. The transducer array of any one of illustrative embodiments 64-75, wherein the non-hydrogel adhesive-free skin-interface material is a nonconductive material with a conductive material suspended therein.

79. The transducer array of illustrative embodiment 78, wherein the nonconductive material is a skin mask and the conductive material is conductive particles.

80. An electronic apparatus comprising:

an electric field generator comprising circuitry configured to generate an alternating current electrical signal having an alternating current waveform;

a first conducting lead connected to the electric field generator so as to receive the alternating current electrical signal;

a second conducting lead connected to the electric field generator so as to receive the alternating current electrical signal;

a first transducer array connected to the first conducting lead;

a second transducer array connected to the second conducting lead;

wherein the first transducer array comprises:

an electrode layer comprising one or more electrode; and a non-hydrogel adhesive-free skin-interface material for placement between a surface of the electrode layer and a patient's skin, the non-hydrogel adhesive-free skin-interface material being configured to contact the patient's skin and to conform to contours and/or irregularities of the patient's skin.

81. The electronic apparatus of illustrative embodiment 80, wherein the non-hydrogel adhesive-free skin-interface material is a conductive material, and further comprising a DC blocking capacitor in series with the first conducting lead.

82. The electronic apparatus of illustrative embodiment 81, wherein the DC blocking capacitor is a first DC blocking capacitor, and further comprising a second DC blocking capacitor in series with the second conducting lead.

83. The electronic apparatus of illustrative embodiment 80, wherein the non-hydrogel adhesive-free skin-interface material is a nonconductive material with a conductive material suspended therein.

From the above description, it is clear that the inventive concepts disclosed and claimed herein are well adapted to carry out the objects and to attain the advantages mentioned herein, as well as those inherent in the invention. While exemplary implementations of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A transducer array for generating a Tumor Treating Field (TTField) for the treatment of a cancer or tumor of a patient, the transducer array comprising:

an electrode assembly including an electrode layer comprising one or more electrode, the one or more electrode configured to receive an alternating current waveform having a frequency in a range from 50 kHz to 1 MHz and induce the tumor treating field (TTField) to treat the cancer or tumor; and a non-hydrogel adhesive-free skin-interface material for placement between a surface of the electrode layer and the patient's skin, the non-hydrogel adhesive-free skin-interface material being configured to contact the patient's skin and to conform to contours and/or irregularities of the patient's skin.

2. The transducer array of claim 1, wherein the non-hydrogel adhesive-free skin-interface material is a viscoelastic material.

3. The transducer array of claim 1, wherein the non-hydrogel adhesive-free skin-interface material comprises a silicone polymer.

4. The transducer array of claim 1, further comprising a covering layer disposed on an outwardly facing surface of the electrode layer, the covering layer extending laterally beyond at least a portion of a perimeter of the electrode layer such that at least a portion of the covering layer is in contact with the non-hydrogel adhesive-free skin-interface material or the patient's skin, and, optionally, wherein the covering layer is an adhesive tape or bandage.

5. The transducer array of claim 1, wherein the non-hydrogel adhesive-free skin-interface material is a conductive material.

6. The transducer array of claim 5, wherein there is no insulating dielectric layer disposed between the electrodes and the patient's skin.

7. The transducer array of claim 1, wherein the non-hydrogel adhesive-free skin-interface material is a nonconductive material with a conductive material suspended therein.

8. The transducer array of claim 7, wherein the non-hydrogel adhesive-free skin-interface material comprises a silicone polymer with conductive carbon particles suspended therein.

9. The transducer array of claim 8, further comprising an intermediate layer, which is a conductive material, between the electrode layer and the non-hydrogel adhesive-free skin interface material.

10. The transducer array of claim 9, wherein the intermediate layer is a conductive fabric.

11. The transducer array of claim 7, wherein the nonconductive material is a skin mask and the conductive material is conductive particles.

12. An electronic apparatus for treating a cancer or tumor of a patient, the apparatus comprising:

an electric field generator comprising circuitry configured to generate an alternating current electrical signal having an alternating current waveform having a frequency in a range from 50 kHz to 1 MHZ;

a first conducting lead connected to the electric field generator so as to receive the alternating current electrical signal;

a second conducting lead connected to the electric field generator so as to receive the alternating current electrical signal;

a first transducer array connected to the first conducting lead;

a second transducer array connected to the second conducting lead;

wherein the first transducer array comprises:

an electrode layer comprising one or more electrode configured to receive the alternating current electrical signal having the alternating current waveform having the frequency in the range from 50 kHz to 1 MHz via the first conducting lead and to induce a Tumor Treating Field (TTField) to treat the cancer or tumor; and a non-hydrogel adhesive-free skin-interface material for placement between a surface of the electrode layer and the patient's skin, the non-hydrogel adhesive-free skin-interface material being configured to contact the patient's skin and to conform to contours and/or irregularities of the patient's skin.

13. The electronic apparatus of claim 12, wherein the non-hydrogel adhesive-free skin-interface material is a viscoelastic material.

14. The electronic apparatus of claim 12, wherein the non-hydrogel adhesive-free skin-interface material is a nonconductive material with a conductive material suspended therein.

15. The electronic apparatus of claim 14, wherein the non-hydrogel adhesive-free skin-interface material comprises a silicone polymer with conductive carbon particles suspended therein.

16. The electronic apparatus of claim 15, further comprising an intermediate layer, which is a conductive material, between the electrode layer and the non-hydrogel adhesive-free skin interface material.

17. The electronic apparatus of claim 16, wherein the intermediate layer is a conductive fabric.

18. The electronic apparatus of claim 14, wherein the nonconductive material is a skin mask and the conductive material is conductive particles.

* * * * *